US012648743B2

(12) United States Patent (10) Patent No.: US 12,648,743 B2
Allen et al. (45) Date of Patent: Jun. 9, 2026

(54) ANATOMIC POSITIONING DEVICE

(71) Applicant: See-7 LLC, Casper, WY (US)

(72) Inventors: Cameron Allen, Casper, WY (US);
Seth Allsop, Casper, WY (US)

(73) Assignee: See-7 LLC, Casper, WY (US)

( * ) Notice: Subject to any disclaimer, the term of this
patent is extended or adjusted under 35
U.S.C. 154(b) by 153 days.

(21) Appl. No.: 18/597,049

(22) Filed: Mar. 6, 2024

(65) Prior Publication Data

US 2024/0298978 A1 Sep. 12, 2024

Related U.S. Application Data

(60) Provisional application No. 63/451,286, filed on Mar.
10, 2023.

(51) Int. Cl.
A61B 6/04 (2006.01)
A61B 6/50 (2024.01)

(52) U.S. Cl.
CPC ............ A61B 6/0421 (2013.01); A61B 6/505
(2013.01)

(58) Field of Classification Search
CPC .............................. A61B 6/0421; A61B 6/505
See application file for complete search history.

(56) References Cited

U.S. PATENT DOCUMENTS

| | | | |
|---|---|---|---|
| 1,277,009 A | * | 8/1918 | Weldon .................... A61H 3/02 |
| | | | 135/65 |
| 7,921,490 B2 | | 4/2011 | Kinmon |
| 8,510,882 B2 | | 8/2013 | Campagna et al. |
| 8,544,471 B2 | * | 10/2013 | Campagna ........... A61B 6/0421 |
| | | | 128/845 |
| 9,980,867 B2 | * | 5/2018 | Russell ............... A61G 13/124 |
| 10,478,364 B2 | | 11/2019 | Fossez et al. |
| 2007/0144530 A1 | | 6/2007 | McGinnis et al. |
| 2010/0179604 A1 | | 7/2010 | Campagna et al. |
| 2012/0260923 A1 | | 10/2012 | Campagna |
| 2012/0271142 A1 | | 10/2012 | Campagna |

FOREIGN PATENT DOCUMENTS

| | | | |
|---|---|---|---|
| WO | 2009054850 A1 | 4/2009 | |
| WO | 2009102332 A1 | 8/2009 | |
| WO | 2011139924 A2 | 11/2011 | |
| WO | WO-2014193739 A1 * | 12/2014 | ......... A61G 13/0072 |

OTHER PUBLICATIONS

International Search Report and Written Opinion issued for PCT
Application No. PCT/US2024/018820 on Jul. 3, 2024.

* cited by examiner

*Primary Examiner* — Uzma Alam
*Assistant Examiner* — Fani Polyzos Boosalis
(74) *Attorney, Agent, or Firm* — Austin Rapp

(57) ABSTRACT
An anatomic positioning device is described. The anatomic
positioning device includes a shoulder member, a handle,
and two supports disposed between the shoulder member
and the handle to connect the shoulder member to the
handle.

13 Claims, 8 Drawing Sheets

802

Position a subject on a table for an imaging procedure

804

Move the shoulders of the subject to not obstruct a view of a cervical spine using a pair of mobile shoulder positioners

806

Acquire a lateral radiographic image of the cervical spine

800

ANATOMIC POSITIONING DEVICE

RELATED APPLICATIONS

This application is related to and claims priority from U.S. Provisional Patent Application No. 63/451,286, entitled "CERVICAL RADIOLUCENT MOBILITY ASSIST DEVICE USED TO ENHANCE VISUALIZATION OF KEY STRUCTURES IN THE CERVICAL SPINE," filed on Mar. 10, 2023, which is hereby incorporated by reference herein, in its entirety.

TECHNICAL FIELD

The present disclosure relates generally to medical equipment. More specifically, the present disclosure relates to an anatomic positioning device.

BACKGROUND

The cervical spine is part of the human spinal column located within the neck region. This segment of the spine is responsible for supporting the skull, facilitating a broad range of head movements, and safeguarding the cervical part of the spinal cord. In addition, the cervical spine houses pathways critical for blood flow to the brain and contains nerve roots that extend to various parts of the upper body, underscoring its significance in both the structural and functional aspects of a person's neck and overall bodily coordination and health.

Medical imaging technologies, including radiography (e.g., X-Ray, fluoroscopy, CT, MRI), play a pivotal role in the diagnosis and treatment of various conditions, particularly those involving the cervical spine. These imaging modalities are essential for visualizing the vertebrae to guide medical procedures accurately, especially surgeries. Accurate visualization is crucial for diagnosing conditions, planning surgical interventions, and monitoring post-operative recovery. The cervical spine necessitates precise imaging to avoid any complications that could arise from misinterpretation of the images.

Current systems and methods for positioning patients during radiographic imaging of the cervical spine still have shortcomings. Systems and methods that improve the visualization of the cervical spine may be beneficial.

DETAILED DESCRIPTION

Figure 1:
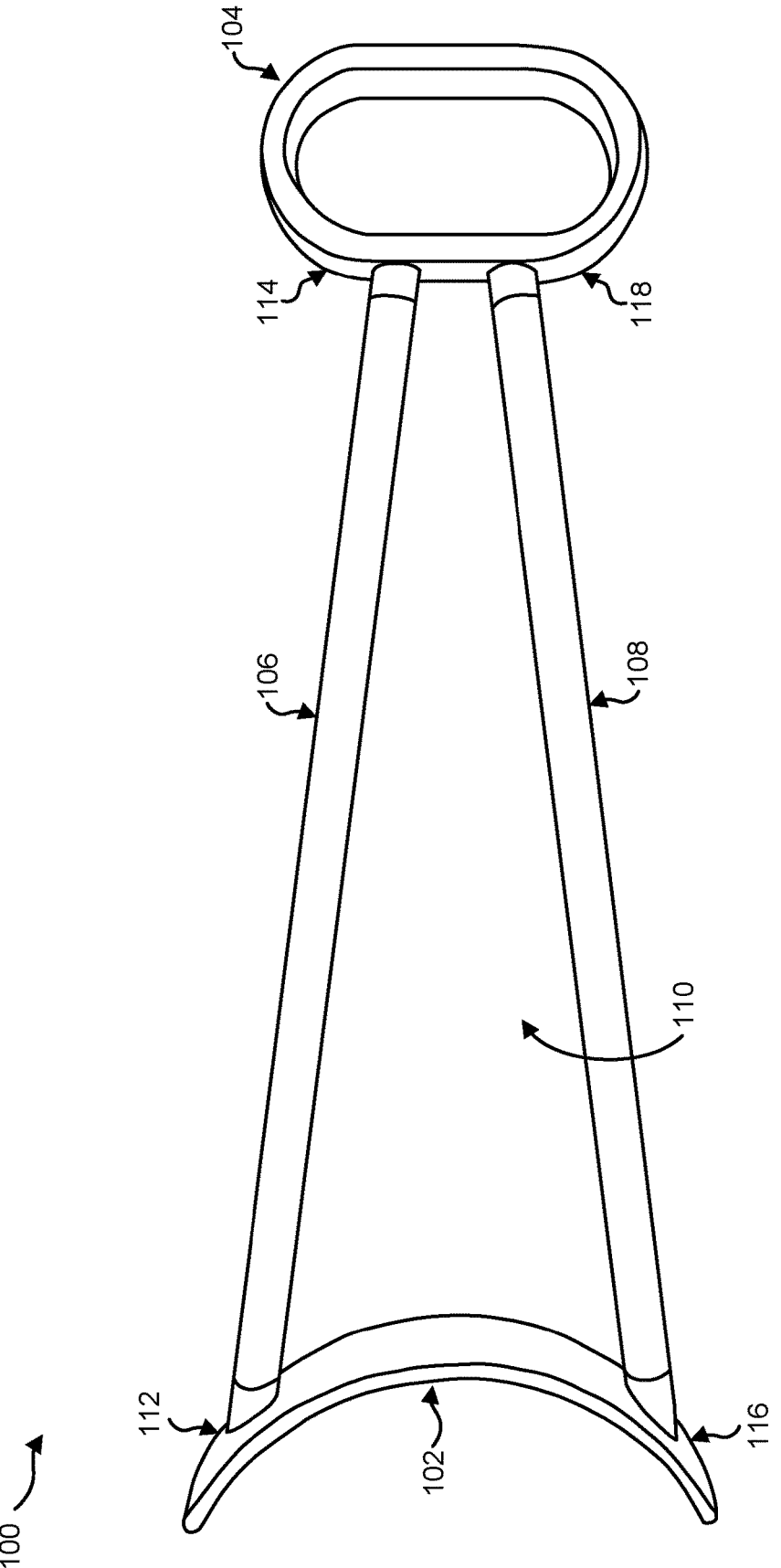
FIG. 1 illustrates a side elevational view of an embodiment of an anatomic positioning device.

An anatomic positioning device is described. The anatomic positioning device includes a shoulder member, a handle, and two supports disposed between the shoulder member and the handle to connect the shoulder member to the handle.

The two supports may form a void between the two supports. In some examples, the two supports may form an A frame defining an unobstructed view between the two supports.

In one embodiment, the two supports may be comprised of a first support connecting an upper portion of the shoulder member to an upper handle portion, and a second support connecting a lower portion of the shoulder member to a lower handle portion. The distance between the upper portion of the shoulder member and the lower portion of the shoulder member may be greater than the distance between an upper handle portion and a lower handle portion. The angle formed between the first support and the second support may be configured to be within a range of 5 degrees to 30 degrees.

In some examples, the shoulder member may be configured in an arcuate form. In some embodiments, the shoulder member may include an elongated end designed for placement under a subject to maintain the apparatus in a stable position.

In still further embodiments, the apparatus may include a lateral positioning member attached to the shoulder member to assist placement of the shoulder member.

An apparatus for anatomic positioning during a radiographic imaging procedure is also disclosed. The apparatus includes a first mobile shoulder positioner, and a second mobile shoulder positioner. Each mobile shoulder positioner may include a shoulder member, a handle, and two supports disposed between the shoulder member and the handle to connect the shoulder member to the handle.

In some examples, the apparatus is configured for intermittent manual pressure. The first mobile shoulder positioner may be independently movable from the second shoulder positioner. Furthermore, the first mobile shoulder positioner may be independently movable in any direction. In one embodiment, the first mobile shoulder positioner and second mobile shoulder positioner are free from any table attachment connectors. In other words, in some embodiments the first mobile shoulder positioner and second mobile shoulder positioner do not have any table attachment connectors.

A method of using anatomic positioning during a radiographic imaging procedure is also described. The method includes positioning a subject on a table for an imaging procedure. The method further includes moving shoulders of the subject to not obstruct a view of a cervical spine using a pair of mobile shoulder positioners. The method also includes acquiring a lateral radiographic image of the cervical spine.

Obtaining clear and unobstructed images of the cervical vertebrae presents unique challenges. A common obstacle encountered during the lateral imaging of the cervical spine is the obstruction caused by the subject's shoulders. This obstruction can impede the clarity and usefulness of the images, as the shoulders may obscure essential details of the vertebrae. The ability to accurately visualize the cervical spine without interference is imperative for successful diagnostic and surgical outcomes.

Current techniques for positioning patients during radiographic imaging of the cervical spine have attempted to mitigate this issue, yet they often fall short of providing an optimal solution. Herein devices, systems, and methods that improve the visualization of the cervical spine are provided.

FIG. 1 illustrates a side elevational view of an embodiment of an anatomic positioning device. In one embodiment, the anatomic positioning device is a shoulder positioner 100. The shoulder positioner 100 may be a mobile or portable device, which means it is not limited to the use case of being mounted to a ridged surface such as a patient table or bed. Furthermore, the positioner 100 may be lightweight and compact, enabling it to be easily carried by a health care professional from one location to another within a medical facility. In current design, the shoulder positioner 100 may be easily stored in a drawer or cabinet taking up minimal space. The mobility of the positioner 100 makes the product more versatile in a surgery/imaging situation.

In some examples, the shoulder positioner 100 includes a shoulder member 102, a handle 104, and two supports 106, 108 disposed between the shoulder member 102 and the handle 104 to connect the shoulder member 102 to the handle 104. The two supports may comprise a first support 106 and a second support 108.

The shoulder positioner 100 components may be attached together in a modular fashion. This modularity may be achieved through the use of fasteners, snap-fit mechanisms, or other joining methods that enable quick assembly and disassembly. This feature not only simplifies the manufacturing and maintenance processes but also enhances the device's versatility, as components can be easily replaced or modified as required.

In other implementations, the shoulder positioner 100 may be constructed as an integrated unit, where the shoulder member 102, handle 104, and supports 106, 108 are formed together in a single manufacturing process. This approach ensures seamless integration of components for enhanced structural integrity and durability. The integrated design may be particularly beneficial for standardizing the device for common imaging procedures, ensuring consistent performance and ease of use.

The shoulder positioner 100 may be used as a cervical radiolucent mobility assist device to enhance visualization of structures in the cervical spine. As will be described and illustrated below, the shoulder positioner 100 may be used in pairs with each unit 100 being used on the upper extremities of a patient which includes, but is not limited to, the neck and shoulders of a patient during spinal surgery.

The shoulder member 102 may be formed to engage the shoulder of a patient. In some examples, the shoulder member 102 may be curved to substantially fit the contour of the shoulder. In other words, the shoulder member 102 may be configured in an arcuate form.

The supports 106, 108 may be in the form of tubes or shafts. In some implementations, the supports 106, 108 may be substantially straight. The tubular or shaft-like configuration is engineered to provide the necessary rigidity to maintain the structural integrity of the shoulder positioner 100 under the load conditions typically encountered during use, without adding unnecessary bulk or weight.

The handle 104 is used by a health care provider to manipulate the shoulder positioner 100. The health care provider may use the positioner 100 and apply pressure to increase visibility of the cervical spine during a radiographic imaging procedure. Various alternative embodiments of the handle 104 may be implemented to be more ergonomic, anatomically designed, easier to grip or easier to manufacture. For example, the handle 104 may be an oval, a handle grip, or variations thereof.

The shoulder positioner 100 may be made from radiolucent materials allowing it to be invisible or substantially invisible to imaging (x-ray, fluoroscopy, Computed Tomography (CT), Magnetic Resonance Imaging (MRI) or similar). For example, the shoulder positioner 100 may be made from materials such as aluminum, carbon fiber, fiberglass, glass, plastic, PEEK, polycarbonate, fabric, webbing, or any other radiolucent under medical imaging and/or ecologically friendly.

The two supports 106, 108 may be placed to form a void 110 between the two supports 106, 108. The void 110 is an open space between the supports 106, 108 and between the handle 104 and the shoulder member 102. In some implementations, the void 110 may span from handle 104 to the shoulder member 102 and from the first support 106 to the second support 108 such that no part of the shoulder positioner 100 is in the void 110. In some examples, the two supports 106, 108 form an A frame defining an unobstructed view between the two supports 106, 108.

The first support 106 may connect an upper portion 112 of the shoulder member 102 to an upper handle portion 114. The second support 108 may connect a lower portion 116 of the shoulder member 102 to a lower handle portion 118. In some examples, the distance between the upper portion 112 of the shoulder member 102 and the lower portion 116 of the shoulder member 102 is greater than the distance between an upper handle portion 114 and a lower handle portion 118. The angle formed between the first support 106 and the second support 108 may be configured to be within a range of five degrees to 30 degrees.

In one implementation, the first support 106 and the second support 108 may be substantially similar such that the supports are interchangeable. Such an implementation may be beneficial in manufacturing and construction. In other embodiments, the first support 106 and the second support 108 may be different.

In the embodiment of FIG. 1, the shoulder positioner 100 is horizontally symmetrical, meaning that its structure can be divided into two mirror-image halves along a horizontal axis. This symmetrical design provides upper and lower portions of the device 100 that are identical in shape and functionality. Such symmetry helps stabilize the positioner 100 during use, allowing for an even distribution of weight and pressure, which is particularly beneficial when positioning patients for radiographic imaging. The horizontal symmetry may also simplify the manufacturing and assembly process of the positioner 100.

Figure 2:
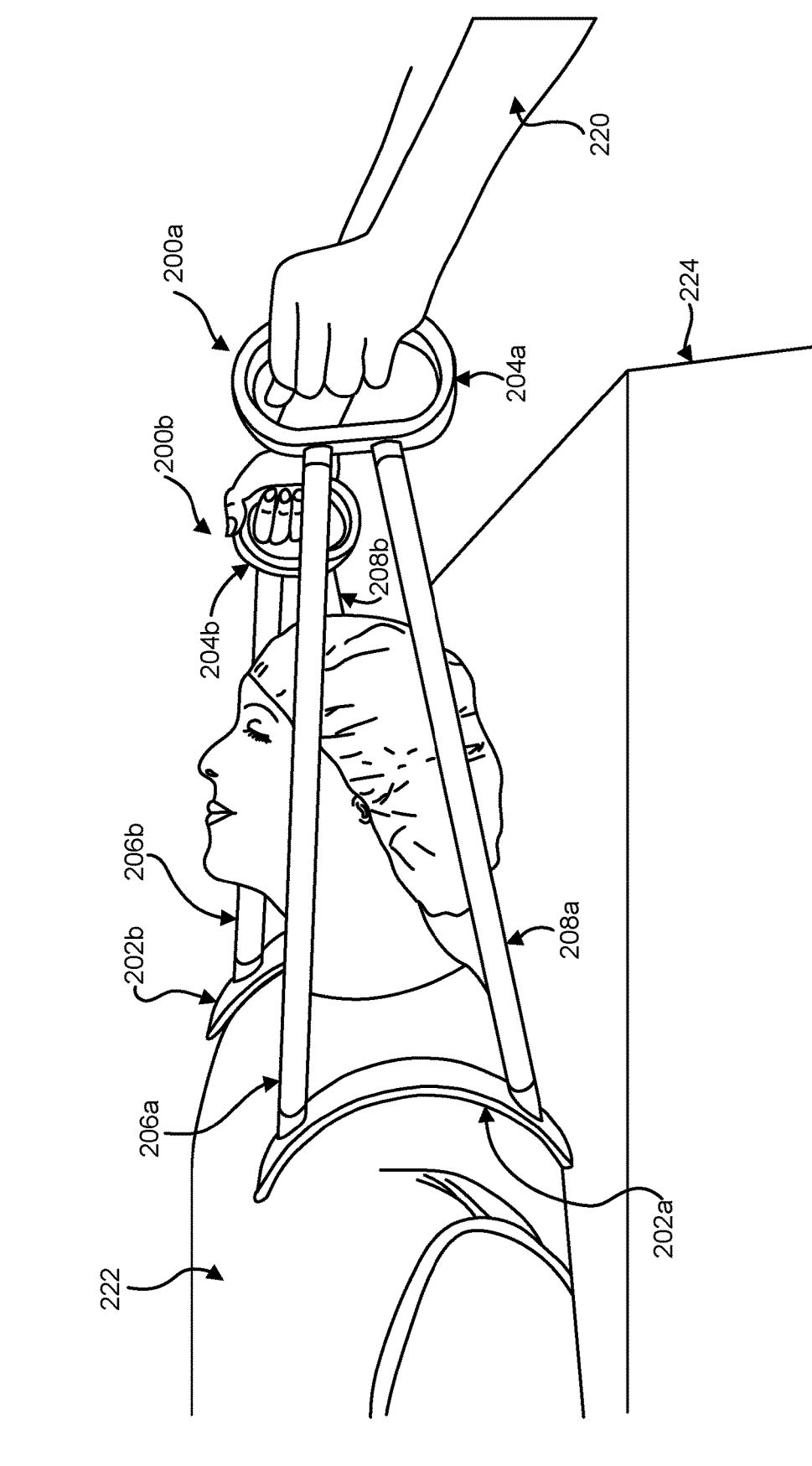
FIG. 2 illustrates a perspective view of anatomic positioning devices being used with a patient in a supine position.

FIG. 2 illustrates a perspective view 200 of anatomic positioning devices being used with a patient 222 in a supine position on a table 224 during a radiographic imaging procedure. A health care provider 220 uses a first mobile shoulder positioner 200a and a second mobile shoulder positioner 200b. The first mobile shoulder positioner 200a and the second mobile shoulder positioner 200b may be similar to the shoulder positioner 100 illustrated and described in FIG. 1. In some examples, the first mobile shoulder positioner 200a and the second mobile shoulder positioner 200b may be substantially similar such that they can be used interchangeably on either side of the patient 222.

The first mobile shoulder positioner 200a may include a shoulder member 202a, a handle 204a, and two supports 206a, 208a disposed between the shoulder member 202a and the handle 204a to connect the shoulder member 202a to the handle 204a.

The second mobile shoulder positioner 200b may include a shoulder member 202b, a handle 204b, and two supports 206b, 208b disposed between the shoulder member 202b and the handle 204b to connect the shoulder member 202b to the handle 204b.

The positioners 200a, 200b may be placed in the area between the neck and lateral shoulder of the patient 222 to provide variable (as needed) caudal (toward the feet) pressure thereby exposing the cervical spine to increase visualization of spine imaging. This application of pressure is not arbitrary but is carefully calibrated by the health care provider 220 to gently displace soft tissue and reduce interference from the shoulder area, thereby enhancing the exposure of the cervical spine. The ultimate aim of this targeted pressure application is to improve the visualization of the cervical spine during imaging processes. This enhancement is for obtaining clearer, more detailed images of the spine and will assist in providing a more accurate diagnosis, treatment planning, and monitoring of spinal conditions.

In such a configuration, the positioners 200a, 200b may be used for intermittent manual pressure by the health care provider 220. The first mobile shoulder positioner 200a is independently movable from the second shoulder positioner 200b. In addition, the first mobile shoulder positioner 200a is independently movable in any direction. In the embodiment shown in FIG. 2, there is no connection between the first mobile shoulder positioner 200a and the second mobile shoulder positioner 200b. Furthermore, the first mobile shoulder positioner 200a and second mobile shoulder positioner 200b are free from any table attachment connectors.

Figure 3:
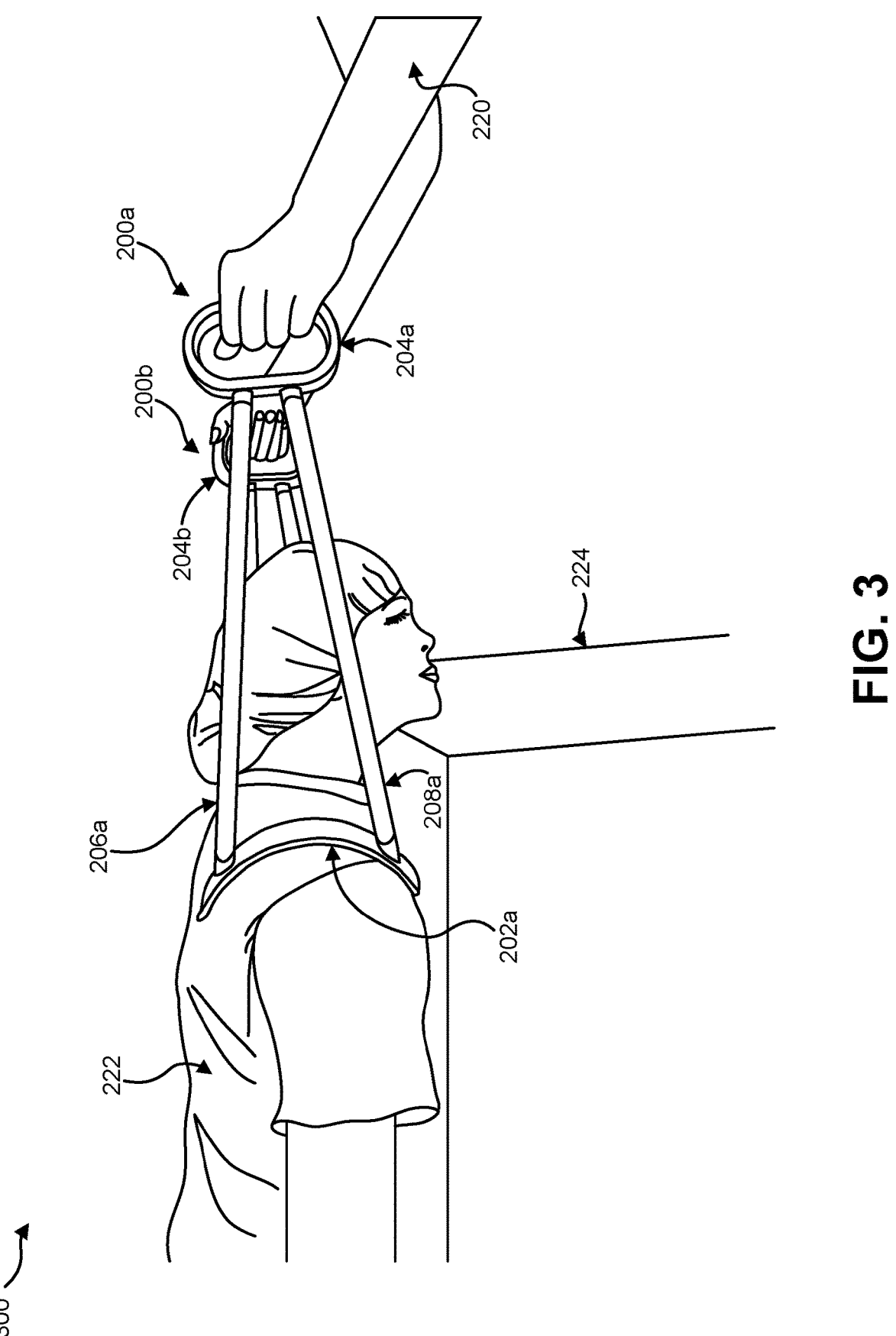
FIG. 3 illustrates a perspective view of anatomic positioning devices being used with a patient in a prone position.

FIG. 3 illustrates a perspective view 300 of anatomic positioning devices being used with the patient 222 in a prone position on a table 224 during a radiographic imaging procedure. FIG. 3 illustrates a scenario similar to that depicted in FIG. 2, with the exception that the patient 222 is now in a prone position on the table 224. The health care provider 220 utilizes the same mobile shoulder positioners 200a, 200b for the radiographic imaging procedure, adapted appropriately to accommodate the patient's prone orientation. The positioners 200a, 200b may be placed between the neck and lateral shoulder of the patient 222 to provide variable caudal pressure thereby exposing the cervical spine of the patient 222 for increased visualization of spine imaging.

Figure 4:
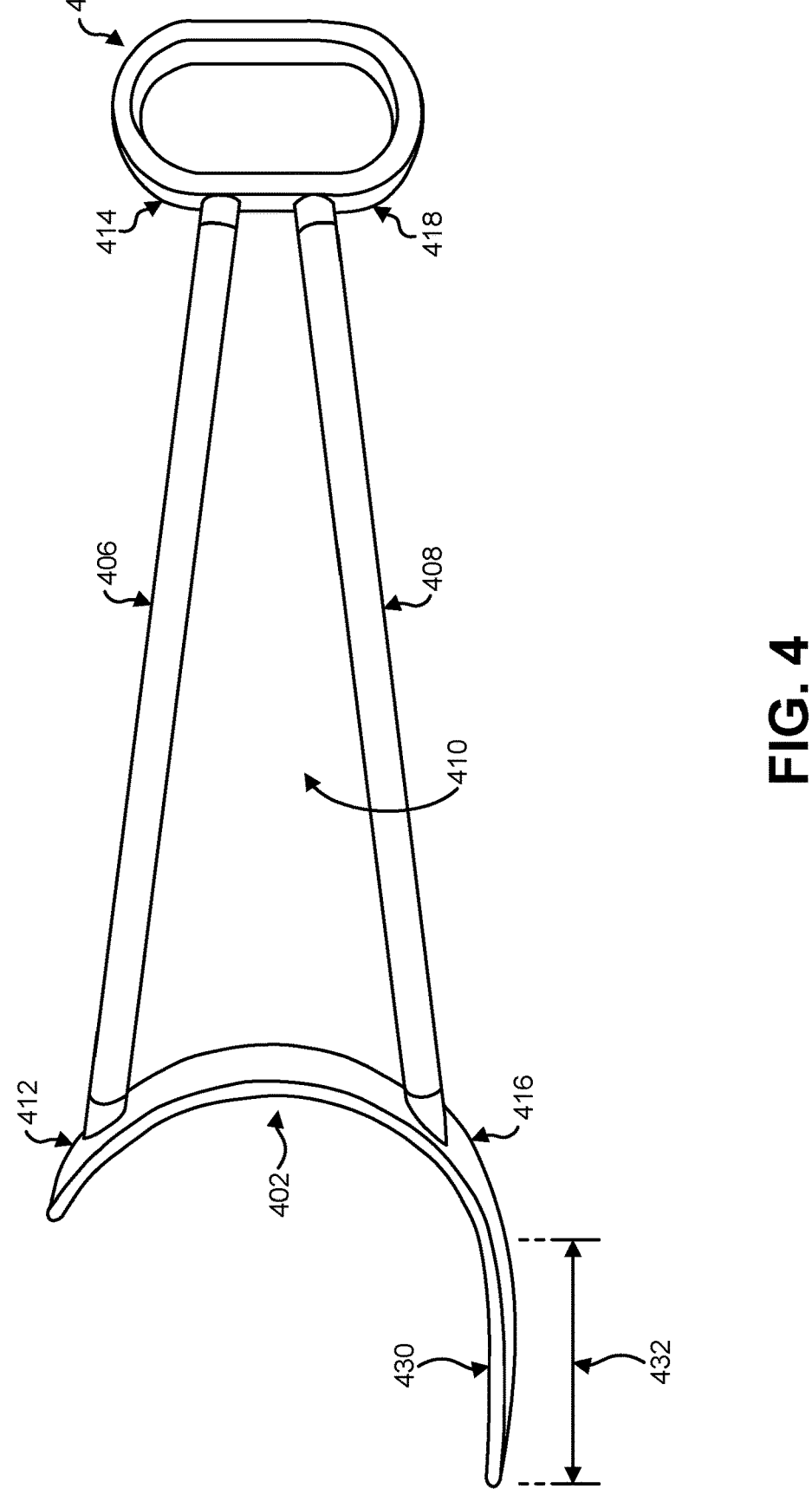
FIG. 4 illustrates a side elevational view of another embodiment of an anatomic positioning device.

FIG. 4 illustrates a side elevational view of another embodiment of a shoulder positioner 400. The shoulder positioner 400 includes a shoulder member 402, a handle 404, and two supports 406, 408 disposed between the shoulder member 402 and the handle 404 to connect the shoulder member 402 to the handle 404. The two supports may comprise a first support 406 and a second support 408.

The two supports 406, 408 may be placed to form a void 410 between the two supports 406, 408. The void 410 is an open space between the supports 406, 408 and between the handle 404 and the shoulder member 402. In some examples, the two supports 406, 408 form an A frame defining an unobstructed view between the two supports 406, 408.

The first support 406 connects an upper portion 412 of the shoulder member 402 to an upper handle portion 414. The second support 408 connects a lower portion 416 of the shoulder member 402 to a lower handle portion 418.

In the embodiment shown in FIG. 4, the shoulder member 402 is configured in an arcuate form and further includes an elongated end 430 designed for placement under a patient to maintain the apparatus 400 in a stable position. The elongated end 430 may be formed to slide under the patient's body, and more specifically the patient's shoulder. This feature uses the patient's own weight to secure the apparatus 400 in a stable and fixed position throughout its use. The elongated end 430 may serve a dual purpose: not only does it anchor the apparatus 400 firmly in place, thereby mitigating the risk of displacement during movements, but it also ensures that the apparatus 400 may remain undisturbed and functional during various medical procedures, including surgeries where stability and precision are paramount.

In some examples, the elongated end 430 may extend a distance 432 beyond the end of the shoulder member 102 of FIG. 1. In some examples, the distance 432 is between two and six inches. In further examples, the distance 432 is between three and four inches approximately.

Figure 5:
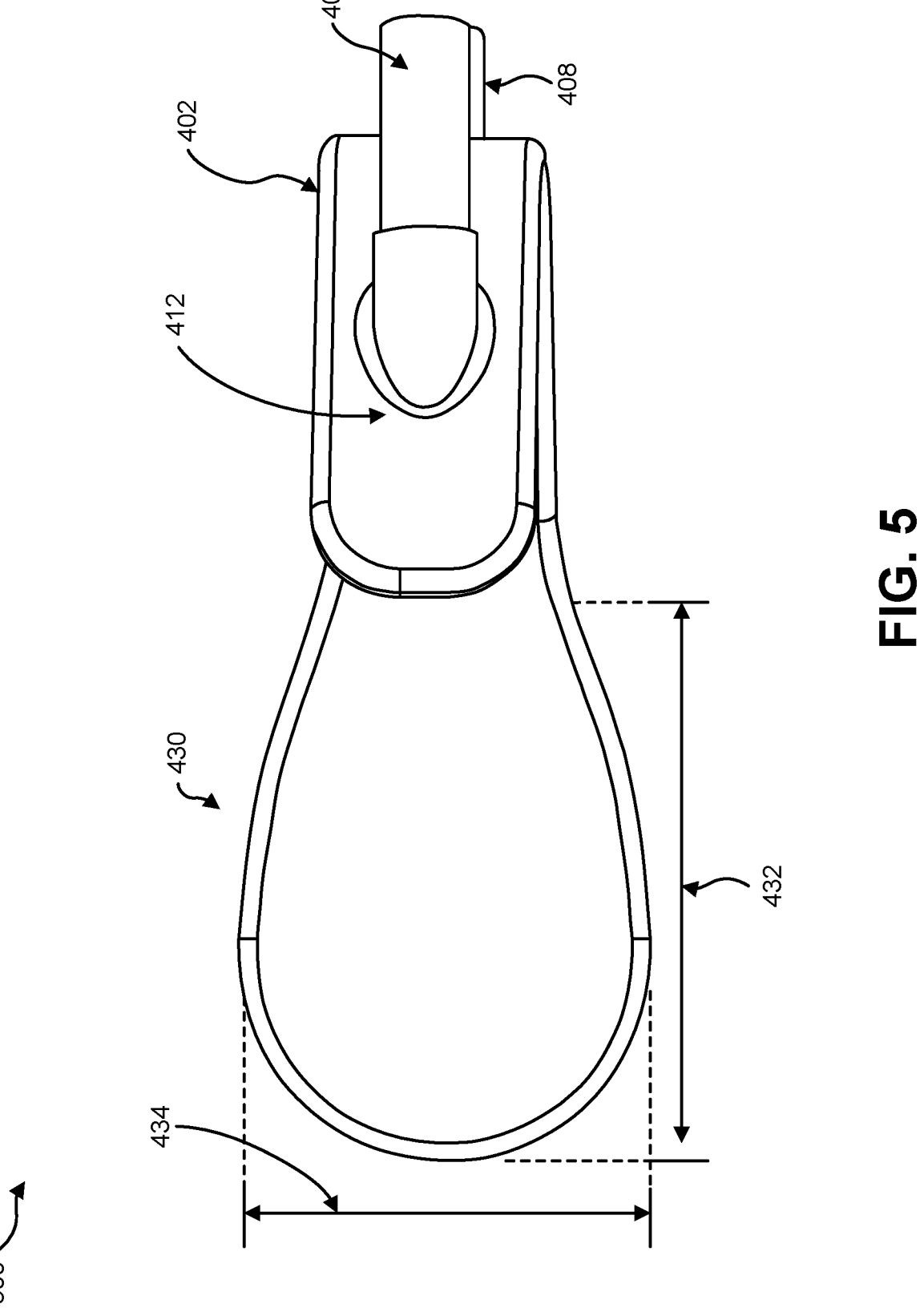
FIG. 5 illustrates a top plan view of the elongated end of the embodiment of FIG. 4.

FIG. 5 illustrates a top plan view 500 of the elongated end 430 of the embodiment of FIG. 4. As shown in the view 500 of FIG. 5, the elongated end 430 may also have a maximum width 434 that is wider than the rest of the shoulder member 402. In some examples, the maximum width 434 of the elongated end 430 may be between 1.5d to 2d, where d is the typical width of the shoulder member 402. The increased length distance 432 and the increased width 434 serve to increase the surface area of the elongated end 430 thereby enhancing the ability of the shoulder positioner 400 to be secured under the patient's shoulders.

Figure 6:
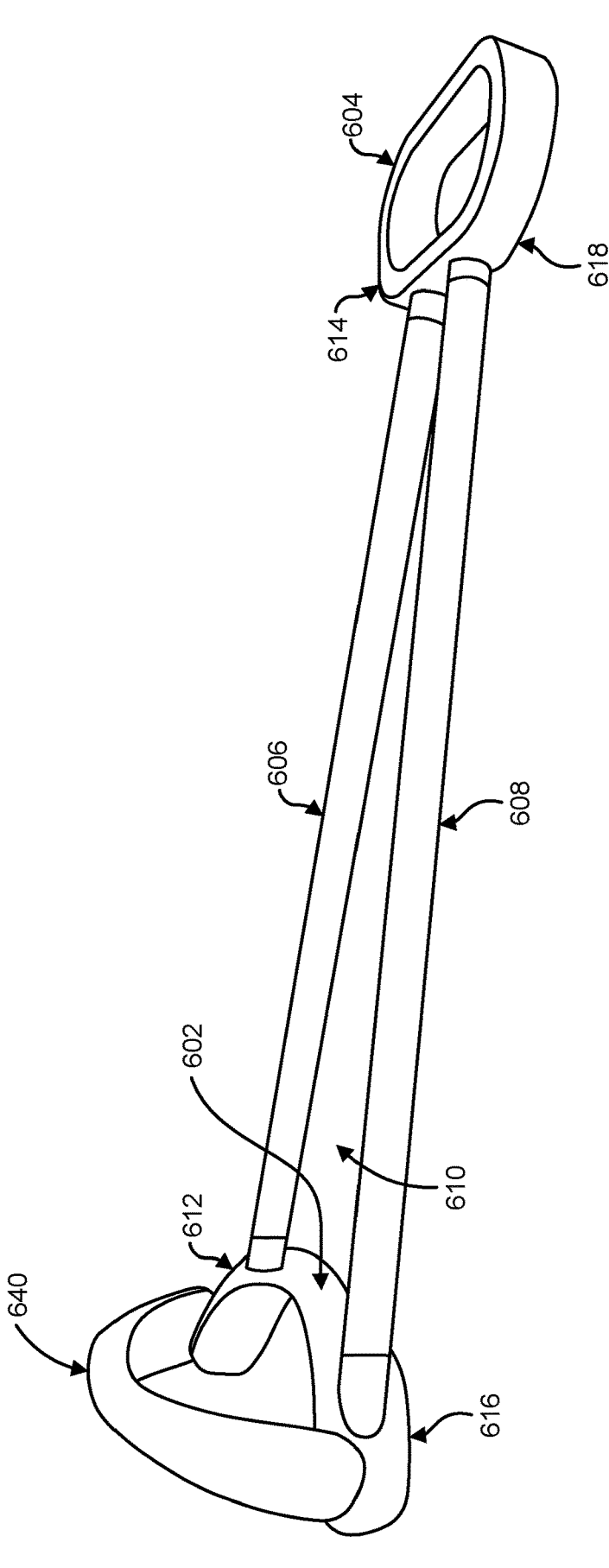
FIG. 6 illustrates a side perspective view of another embodiment of an anatomic positioning device.

FIG. 6 illustrates a side perspective view of another embodiment of an anatomic positioning device. The embodiment of a shoulder positioner 600 illustrates a lateral positioning member 640 attached to the shoulder member 602 to assist placement of the shoulder member 602.

The shoulder positioner 600 includes the shoulder member 602, a handle 604, and two supports 606, 608 disposed between the shoulder member 602 and the handle 604. The two supports 606, 608 form a void 610 between the two supports 606, 608.

The first support 606 connects an upper portion 612 of the shoulder member 602 to an upper handle portion 614. The second support 608 connects a lower portion 616 of the shoulder member 602 to a lower handle portion 618.

In the embodiment shown in FIG. 6, the shoulder member 602 is configured in an arcuate form and further includes a lateral positioning member 640 to maintain the correct lateral placement of the device 600 on the superior shoulder of the patient. The lateral positioning member 640 may be a half circle arch at a 90-degree angle from the shoulder member 602 arch so that is wraps around the lateral outside edge of the patient's shoulder. When the lateral positioning member 640 is engaging the patient's shoulder, a correct lateral placement of the device 600 may be maintained with the patient.

Figure 7:
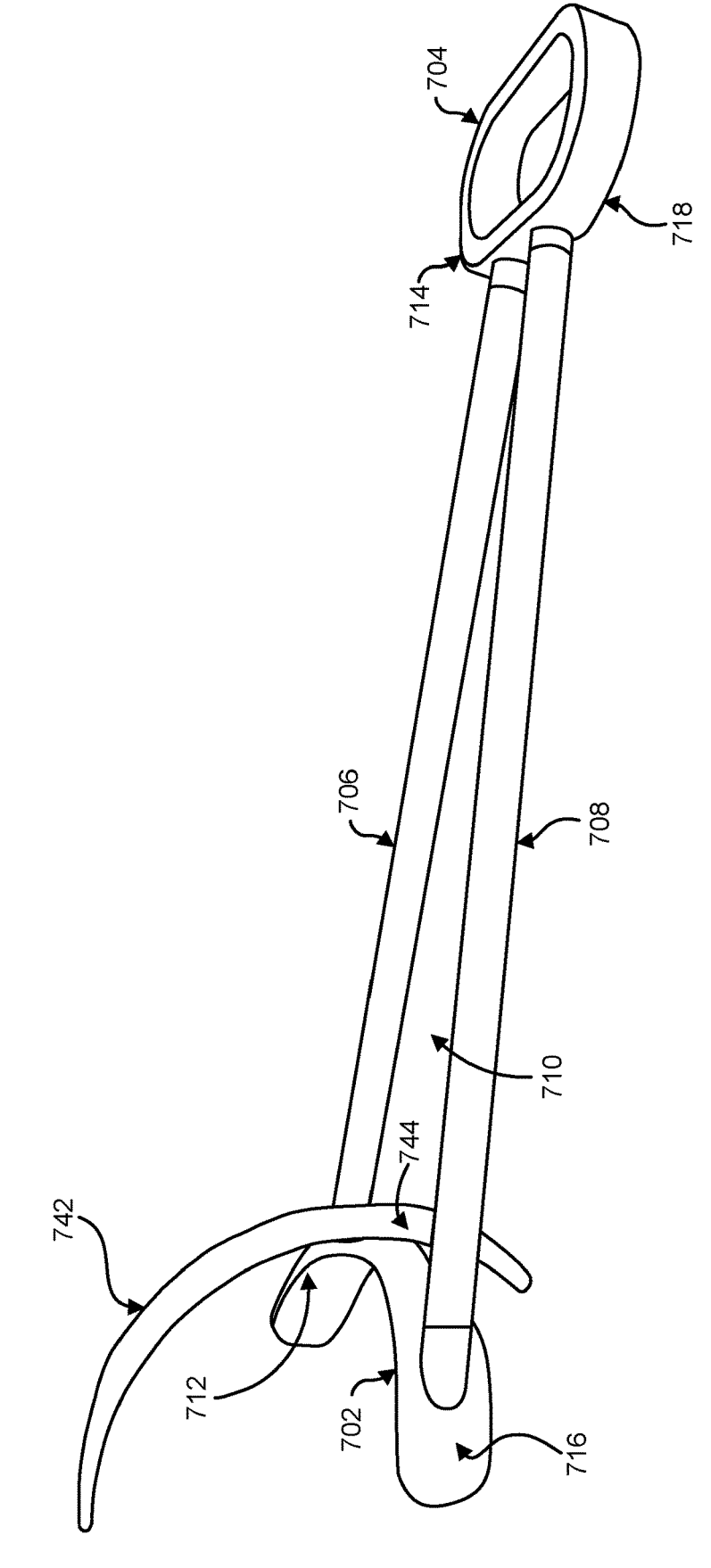
FIG. 7 illustrates a side perspective view of another embodiment of an anatomic positioning device.

FIG. 7 illustrates a side perspective view of another embodiment of an anatomic positioning device. The embodiment of the shoulder positioner 700 in FIG. 7 illustrates another embodiment of a lateral positioning member 742 attached to the shoulder member 702 to assist placement of the shoulder member 702.

The shoulder positioner 700 includes the shoulder member 702, a handle 704, and two supports 706, 708 disposed between the shoulder member 702 and the handle 704. The two supports 706, 708 form a void 710 between the two supports 706, 708.

The first support 706 connects an upper portion 712 of the shoulder member 702 to an upper handle portion 714. The second support 708 connects a lower portion 716 of the shoulder member 702 to a lower handle portion 718.

In the embodiment shown in FIG. 7, the shoulder member 702 is configured in an arcuate form and further includes a lateral positioning member 742 to maintain the correct lateral placement of the device 700 on the superior shoulder of the patient. The lateral positioning member 742 may be a half circle arch connected at one end 744 to the shoulder member 702 arch so that is wraps around the lateral outside edge of the patient's shoulder. The lateral positioning member 742 may be attached at one end 744 to the center of the shoulder member 702 such that it bisects the shoulder member 702. The mechanism of action for the lateral positioning member 742 involves it making contact with the patient's shoulder, leveraging its unique form to secure the device 700 in the correct lateral position. Thus, the lateral positioning member 742 may prevent lateral movement or displacement of the device 700, ensuring that it remains in the optimal position for its intended use. Through this alignment facilitated by the lateral positioning member 742, the device 700 may achieve its purpose without necessitating constant adjustments, thereby enhancing the efficiency of medical procedures and patient comfort.

Figure 8:
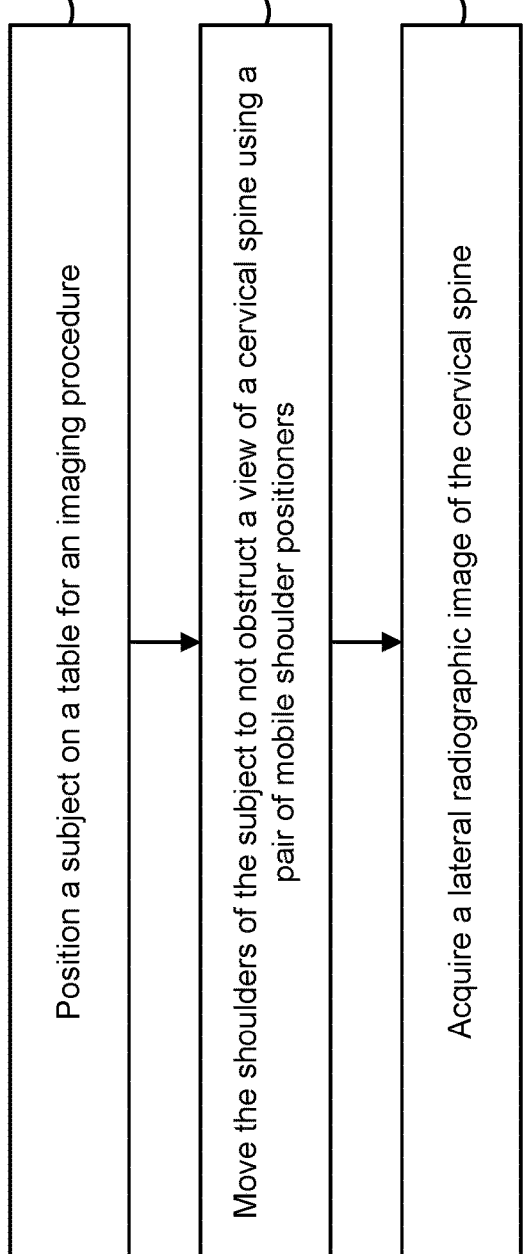
FIG. 8 illustrates a flow diagram of an embodiment of a method for using an anatomic positioning device.

FIG. 8 illustrates a flow diagram of an embodiment of a method 800 for using an anatomic positioning device during a radiographic imaging procedure. Initially, the subject or patient is positioned 802 on a table preparatory for an imaging procedure. This initial positioning may vary, with the patient being placed in either a supine (lying on the back) or prone (lying on the stomach) orientation, depending on the specific requirements of the imaging procedure to be undertaken.

Following the patient's positioning 802, the shoulders of the subject are then moved 804 to not obstruct a view of a cervical spine using a pair of mobile shoulder positioners as described herein. The shoulder positioners are manipulated to adjust the shoulders' position gently, effectively mitigating any potential obstruction that could compromise the clarity and diagnostic utility of the cervical spine images.

Once the shoulders have been moved 804 into position, a lateral radiographic image of the cervical spine is acquired 806. This image acquisition 806 step is improved upon as it harnesses the improved access and visibility afforded by the adjusted shoulder positioning, enabling the generation of high-quality radiographic images. These images are pivotal for the accurate diagnosis, evaluation, and subsequent treatment planning for conditions affecting the cervical spine, illustrating the essential role of the anatomical positioning device in enhancing the effectiveness of radiographic imaging procedures.

As used herein, the term "and/or" should be interpreted to mean one or more items. For example, the phrase "A, B and/or C" should be interpreted to mean any of: only A, only B, only C, A and B (but not C), B and C (but not A), A and C (but not B), or all of A, B, and C. As used herein, the phrase "at least one of" should be interpreted to mean one or more items. For example, the phrase "at least one of A, B and C" or the phrase "at least one of A, B or C" should be interpreted to mean any of: only A, only B, only C, A and B (but not C), B and C (but not A), A and C (but not B), or all of A, B, and C. As used herein, the phrase "one or more of" should be interpreted to mean one or more items. For example, the phrase "one or more of A, B and C" or the phrase "one or more of A, B or C" should be interpreted to mean any of: only A, only B, only C, A and B (but not C), B and C (but not A), A and C (but not B), or all of A, B, and C.

What is claimed is:

1. An apparatus comprising:
   a shoulder member configured to engage a first shoulder of a patient;
   a handle; and
   two supports disposed between the shoulder member and the handle to connect the shoulder member to the handle, wherein the two supports form a void between the two supports and between the shoulder member and the handle;
   wherein the apparatus is configured for intermittent manual caudal pressure; and
   wherein the apparatus is not connected to a second shoulder member that engages a second shoulder of the patient.

2. The apparatus as defined in claim 1, wherein the two supports form an A frame defining an unobstructed view between the two supports.

3. The apparatus of claim 1, wherein the shoulder member is configured in an arcuate form.

4. The apparatus of claim 1, wherein the two supports comprise:
   a first support connecting an upper portion of the shoulder member to an upper handle portion; and
   a second support connecting a lower portion of the shoulder member to a lower handle portion.

5. The apparatus of claim 4, wherein the distance between the upper portion of the shoulder member and the lower portion of the shoulder member is greater than the distance between an upper handle portion and a lower handle portion.

6. The apparatus of claim 5, wherein the angle formed between the first support and the second support is configured to be within a range of 5 degrees to 30 degrees.

7. The apparatus of claim 1, wherein the shoulder member is configured in an arcuate form and further comprises an elongated end designed for placement under a subject to maintain the apparatus in a stable position.

8. The apparatus of claim 1, further comprising a lateral positioning member attached to the shoulder member to assist placement of the shoulder member.

9. An apparatus for anatomic positioning during a radiographic imaging procedure, comprising:
   a first mobile shoulder positioner comprising:
      a first shoulder member configured to engage a first shoulder of a patient;
      a first handle; and
      two first supports disposed between the first shoulder member and the first handle to connect the first shoulder member to the first handle, wherein the two first supports form a first void between the two first supports and between the first shoulder member and the first handle;
   a second mobile shoulder positioner comprising:
      a second shoulder member configured to engage a second shoulder of the patient;
      a second handle; and
      two second supports disposed between the second shoulder member and the second handle to connect the second shoulder member to the second handle, wherein the two second supports form a second void between the two second supports and between the second shoulder member and the second handle;
   wherein the apparatus is configured for intermittent manual caudal pressure; and
   wherein the first mobile shoulder positioner is not connected to the second mobile shoulder positioner.

10. The apparatus as defined in claim 9, wherein the first mobile shoulder positioner is independently movable from the second shoulder positioner.

11. The apparatus as defined in claim 9, wherein the first mobile shoulder positioner is independently movable in any direction.

12. The apparatus as defined in claim 9, wherein the first mobile shoulder positioner and second mobile shoulder positioner are free from any table attachment connectors.

13. A method of using anatomic positioning during a radiographic imaging procedure, comprising:
positioning a subject on a table for an imaging procedure;
 moving shoulders of the subject to not obstruct a view of a cervical spine using a pair of mobile shoulder positioners, wherein each mobile shoulder positioner comprises:
a shoulder member configured to engage only one shoulder of a patient;
  a handle;
  two supports disposed between the shoulder member and the handle to connect the shoulder member to the handle, wherein the two supports form a void between the two supports and between the shoulder member and the handle;
  wherein the pair of mobile shoulder positioners is configured for intermittent manual caudal pressure; and
  wherein the pair of mobile shoulder positioners are independently movable and not connected to each other; and
 acquiring a lateral radiographic image of the cervical spine.

\* \* \* \* \*